United States Patent [19]
Lipsky et al.

[11] Patent Number: 6,138,304
[45] Date of Patent: Oct. 31, 2000

[54] ADJUSTABLE SURGICAL SUPPORT

[76] Inventors: William Lipsky; Sharon D. Lipsky, both of 5802 Picasso, Houston, Tex. 77096-3913

[21] Appl. No.: 09/313,250

[22] Filed: May 18, 1999

[51] Int. Cl.[7] .................................................. A47C 20/02
[52] U.S. Cl. ........................... 5/621; 5/622; 5/623; 5/643
[58] Field of Search ................................ 5/621, 622, 623, 5/630, 636, 646, 643; 248/118, 118.3, 188.5; 128/845, 846

[56] References Cited

U.S. PATENT DOCUMENTS

| | | | |
|---|---|---|---|
| 4,390,011 | 6/1983 | Evans | 248/118 X |
| 4,620,697 | 11/1986 | Pithon | 269/328 |
| 4,681,309 | 7/1987 | Lechner | 5/646 |
| 5,410,769 | 5/1995 | Waterman | 5/646 |
| 5,547,463 | 8/1996 | Hinchiliffe et al. | 5/623 X |

FOREIGN PATENT DOCUMENTS

| | | | |
|---|---|---|---|
| 23 52 026 | 4/1975 | Germany | A61G 13/00 |
| 28 36 646 | 3/1980 | Germany | A61G 15/00 |

*Primary Examiner*—Terry Lee Melius
*Assistant Examiner*—Fredrick Conley
*Attorney, Agent, or Firm*—Howery Simon Arnold & White, LLP

[57] ABSTRACT

An improved surgical support device includes an adjustable hand rest and an adjustable head rest. The hand rest can be adjusted to provide a desired resting position both for a patient's head and for the surgeon's hand or hands. The hand rest has multiple degrees of freedom, allowing the surgeon to adjust the hand rest in the vertical and horizontal position and and to rotate the hand rest about the patient's head. The head rest allows vertical adjustment of the patient's head.

20 Claims, 2 Drawing Sheets

ADJUSTABLE SURGICAL SUPPORT

BACKGROUND OF THE INVENTION

During delicate surgical procedures, e.g., eye operations, some type of support for the surgeon's hands is highly desirable. It is important that the hand holding the scalpel or other surgical instrument has a firm support throughout the procedure, e.g., to permit small and precise incisions to be made.

In the past, many surgical procedures involving the eye were performed from the head of the bed. The surgeon would rest his or her hands on the patient's head while performing the procedure. This provided some stability for the surgeon, but still operating conditions were far from optimal.

In more recent years, various hand rests or supports have been used. These have often involved either utilizing standard operating table equipment or making improvised adaptations of equipment intended for other types of surgical operations. In addition, most of these hand rests were still designed to allow the surgeon to operate while standing at the head of the patient's bed.

Today, surgeons performing eye surgery have found it advantageous to operate from the lateral side, usually on the right or left temporal side of the patient. The prior art equipment has generally not been ideal for the type of delicate surgery that is commonly performed on the eye from the lateral side and could result in the surgeon not making the proper incision or causing injury to the patient.

SUMMARY OF THE INVENTION

The invention relates to an improved surgical support device that may be used by a surgeon. The support device includes an adjustable hand rest and, optionally, an adjustable head rest. The hand rest can be adjusted to provide a desired resting position both for a patient's head and for the surgeon's hand or hands. In some embodiments the hand rest has multiple degrees of freedom, allowing the surgeon to adjust the hand rest in the vertical and horizontal position and and to rotate the hand rest about the patient's head. The optional head rest allows vertical adjustment of the patient's head.

DESCRIPTION OF ILLUSTRATIVE EMBODIMENTS

Figure 1:
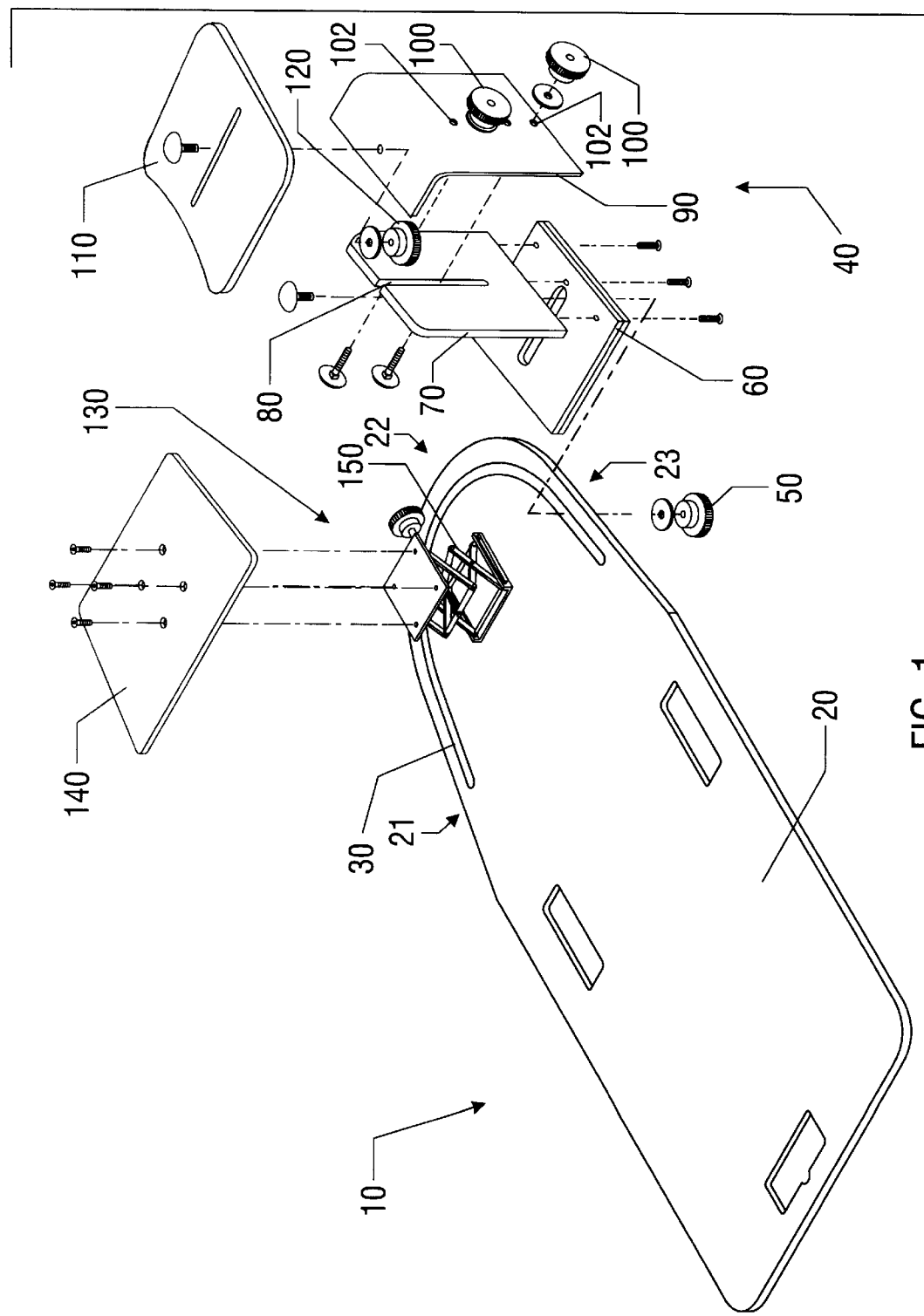
FIG. 1 is an exploded perspective view of one embodiment of a surgical support in accordance with the invention.

Referring to FIG. 1, numeral 10 designates a surgical support in accordance with the invention. The support may be made of any sterilizable material that is suitable for a surgical environment. For example, the support 10 may be made of aluminum, stainless steel, plastic or any other suitable material.

BASE SUPPORT 20: The support 10 includes a base support 20 on which a patient may lie. The base support 20 has a side 21, referred to for convenience as the left side; a head end 22 at which a patient's head will rest; and a side 23, referred to for convenience as the right side. The base support may vary in size and shape.

The base support 20 may be held in place on an operating table by the weight of the patient's body. Alternatively, the base support may be held firmly in place by securing it to the operating table, e.g., with screws, clamps, etc. Often it will be desirable to place a mattress (not shown) over the base support 20 for greater patient comfort.

SLOT 30: The base support 20 contains a curved slot 30 which curves around from the left side 21 of the base support, around the head end 22, to the right side 23. The slot permits adjustable placement of a hand rest assembly at any desired point along the curve as described below.

The slot 30 may pass vertically completely through the base support 20. Alternatively, the slot may pass only part way through the base support, thus taking the form of a groove. As another alternative, the slot 30 may be dispensed with entirely, but it is believed that the support 10 does not work as well without it.

For convenient surgical use as described below, the slot 30 is in the shape of a relatively smooth curve, albeit not necessarily in the shape of an arc of a circle, ellipse, parabola, etc. Alternatively, the slot 30 could take the form of a plurality of straight or semi-straight segments connecting at definite angles, but it is believed that such a form would be less convenient to use.

HAND REST ASSEMBLY 40: A hand rest assembly 40 is secured to the base support 20 so that it can be moved from the left side 21 of the base support, around the head end 22, to the right side 23, and vice versa (referred to for convenience as simply "around the head end 22").

If the slot 30 is present in the base suppot 20, the hand rest assembly 40 may be secured to the base support 20 through the slot 30 by securing means 50. The securing means 50 may take the form of, for example, a hand-operable nut-and-bolt combination. The securing means which allows the surgeon to move the hand rest assembly 40 along the path of the slot and secure the hand rest assembly in place when it is in the desired position.

If the base support 20 does not contain a slot 30, then the hand rest assembly 40 may be secured to the base support by other suitable means, e.g., one or more clamps of suitable strength.

Because the hand rest assembly 40 is capable of being moved around the head end 22, along the path of the slot 30 if the slot is present, the surgeon is able to place the assembly in the desired place around the patient's head. For example, if the surgeon is operating on the left eye, the surgeon can move the hand rest assembly 40 to the left side of the patient (i.e., at the right side 23 of the base support 20), making access to the left eye easier. Then once finished with the left eye, the surgeon can simply slide the adjustable hand rest assembly 40 around the head end 22 to the patient's right side and begin operating on the right eye.

In addition, if the surgeon makes a decision not to use the hand rest assembly 40 in the middle of the operation, he or she can simply slide it around the patient's head and secure it in a spot that is out of the way.

The hand rest assembly 40 may also be used as a work surface during certain operations. For example, when doing corneal transplants the surgeon may operate from the top of the patient's head and desire to support his or her hands on the patient's forehead. In this case, the hand rest assembly 40 provides a close and convenient work surface where the surgeon is able, e.g., to prepare the donor cornea prior to transplanting it.

Figure 2:
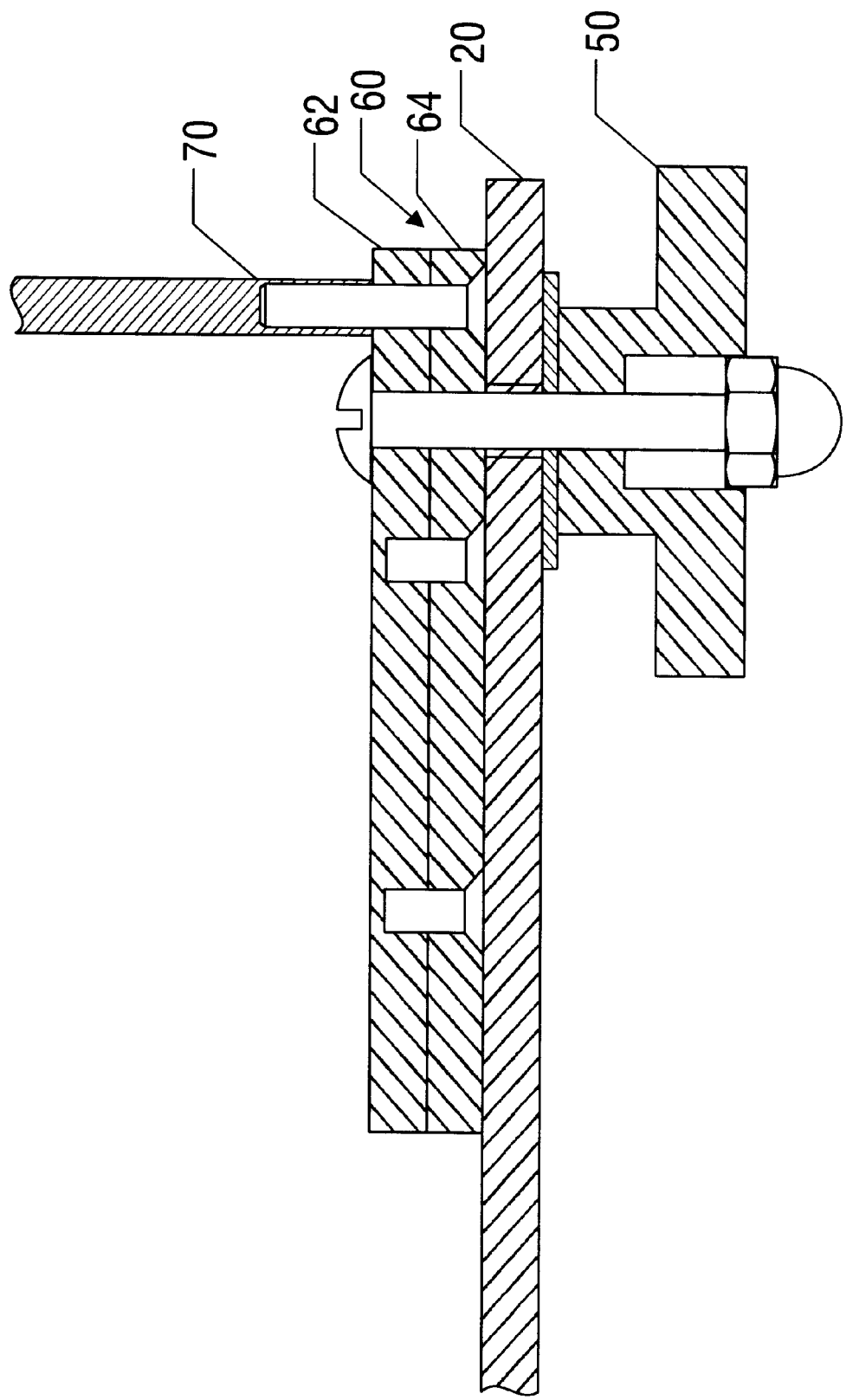
FIG. 2 is a cross-section view of a portion of that embodiment.

In the embodiment shown, the hand rest assembly 40 is vertically adjustable. The assembly includes a base portion 60 that is secured to the base support 20 through the slot 30 in such a manner so as to be movable within the slot. The base support 60 may be lined or coated with a suitable friction-reducing material, e.g., Teflon. Alternatively, as shown in FIG. 2, the base support 60 may comprise an upper plate 62, disposed above a lower plate 64 that is composed of a suitable low-friction material (e.g., Teflon), for easier sliding of the base portion 60 along the slot 30.

A generally-vertical support 70 is secured to the base portion 60 by any convenient manner, e.g., machine screws, adhesives, welding, brazing, etc. The generally-vertical support 70 contains a generally-vertical slot 80.

A generally-vertical adjusting portion 90 is secured to the support 70 through the slot 80 by at least one securing means 100 (e.g., a hand-operable nut-and-bolt combination, possibly including a washer) which allows the surgeon or other user to move the adjusting portion 90 vertically along the path of the slot 80. The portion 90 may include one or more bolt holes 102, through which a bolt may be inserted as part of the securing means 100; four bolt holes 102 are shown in FIG. 1.

The adjusting portion 90 is secured to a generally-horizontal hand rest portion 110 by a securing means 120 (e.g., a hand-operable nut-and-bolt combination) which allows the surgeon to move the hand rest portion 110 in any direction in a generally-horizontal plane. The hand rest portion 110 has a slight concave curve to allow it to be moved slightly closer to the patient's head.

Alternatively, the hand rest assembly 40 may be constructed so that the hand rest portion 110 is kept at a fixed vertical distance from the base support 20.

For some patients, it is easy to get to the head to operate. However, other patients may have a wide body or a narrow head which makes it difficult to get to the head to operate. Optionally, the adjustable hand rest assembly 40 may be implemented to be adjusted in a multitude of directions, allowing the surgeon to place the hand rest portion 110 in the optimum position for operating.

The hand rest portion 110 may be raised or lowered by loosening the securing means 100 and sliding the adjusting portion 90 up or down in the generally-vertical slot 80 in the support 70. When the hand rest portion 110 is at the desired height, the surgeon then tightens the securing means 100 which prevents the hand rest from moving from the desired height.

In addition to moving vertically, the hand rest portion 110 in the embodiment shown is capable of moving in any direction in the generally-horizontal plane. The surgeon can adjust the distance between the hand rest portion 110 and the patient's head by loosening the securing means 120 and sliding the hand rest portion either towards the patient's face or away from it. Once the hand rest portion 110 is at the desired distance from the patient's head, the surgeon then tightens the securing means 120.

In addition to moving towards or away from the patient's head, the hand rest portion 110 can be rotated in a generally-horizontal plane to conform to the curvature of the patient's face. Because the hand rest portion 110 is secured to the adjusting portion 90 by a single securing means 120, it can be rotated clockwise or counterclockwise to conform to the curvature of the patient's head.

Also, the hand rest portion 110 can be rotated in a generally-horizontal plane by loosening the securing means 50 that attaches the base portion 60 to the base support 20 through the slot 30 and rotating the entire hand rest assembly 40 in either the clockwise or counterclockwise direction.

HEAD REST ASSEMBLY 130: The surgical support 10 includes an optional head rest assembly 130. The head rest assembly includes a head rest platform 140 and an adjusting means 150.

The adjusting means 150 may take the form of, e.g., a conventional screw-type jacking device, as shown in FIG. 1, that is manually operable by a hand-turned screw. Other equivalent structure will be readily recognized by those of ordinary skill.

For example, the jacking device may be operated by a small electric motor instead of by a hand-turned screw. Instead of a jacking device, the head rest platform 140 may rest on one or more generally vertical brackets with a series of holes for receiving support pins of the kind commonly used in adjustable shelving.

The adjusting means 150 is secured at one end to the base support 20 and secured at a second end to the head rest platform 140. This allows the surgeon to adjust the height of the patient's head, which rests on the head rest platform, before or during surgical procedures.

Some patients' spines are curved, or their head is back; when their heads are put on the head rest assembly 130, the head is not in the best position for the surgeon to operate. This can be problematic for a surgeon when operating and may cause imprecise incisions. The adjustable head rest assembly 130 addresses this problem because it allows the surgeon to raise or lower the patient's head to a better position.

For clarity, some conventional portions of the surgical support 10 have been omitted from the drawing. While the present invention has been described with reference to the foregoing preferred embodiment, it will be appreciated by those skilled in the art that other changes in form and detail may be made therein without departing from the spirit and scope of the present invention as defined in the appended claims. For example, it will be appreciated by those of ordinary skill, with the hindsight benefit of this disclosure, that the surgical support described above can be used for any surgical procedure in which the surgeon determines that it would be helpful, not just for procedures involving the eye.

What is claimed is:

1. A surgical support comprising:
   a base support upon which a portion of a patient's body weight can rest, and having a left side and a right side with a head end therebetween, and a continuous slot traversing from the left side to the head end and around to the right side; and
   a surgeon's hand rest moveably attached to the base support at the slot such that the hand rest can attach to the base support at any location along the slot.

2. The surgical support of claim 1, wherein the hand rest has freedom of motion selected from the group consisting of: away from and toward the base support, away from and toward a center of the base support, and angled with respect to the base support.

3. The surgical support of claim 1, wherein the hand rest has freedom of motion away from and toward the base support, away from and toward a center of the base support, and angled with respect to the base support.

4. The surgical support of claim 1, wherein the slot is a groove.

5. The surgical support of claim 1, wherein an upper surface of the surgeon's hand rest is substantially planar.

6. The surgical support of claim 1, wherein an upper surface of the surgeon's hand rest is slightly concave.

7. The surgical support of claim 1 wherein the surgeon's hand rest is adapted to support and not impede a surgeon's hand movement during surgery.

8. A surgical support comprising:
   a base support upon which a portion of a patient's body weight can rest, and having a left side and a right side with a head end therebetween, and a continuous slot traversing from the left side to the head end and around to the right side;

a surgeon's hand rest moveably attached to the base support at the slot such that the hand rest can attach to the base support at any location along the slot; and a patient's head rest attached to the base support and comprising a means for adjusting the height of the head rest above the base support.

9. The surgical support of claim 8, wherein the hand rest has freedom of motion selected from the group consisting of: away from and toward the base support, away from and toward a center of the base support, and angled with respect to the base support.

10. The surgical support of claim 8, wherein the hand rest has freedom of motion away from and toward the base support, away from and toward a center of the base support, and angled with respect to the base support.

11. The surgical support of claim 8, wherein the slot is a groove.

12. The surgical support of claim 8, wherein the means for adjusting comprises a jacking device.

13. The surgical support of claim 8, wherein the means for adjusting comprises an adjustable pin and support assembly.

14. The surgical support of claim 8, wherein the means for adjusting is motorized.

15. The surgical support of clam 8 wherein an upper surface of the surgeon's hand rest is substantially planar.

16. The surgical support of claim 8 wherein an upper surface of the surgeon's hand rest is slightly concave.

17. The surgical support of claim 8 wherein the surgeon's hand rest is adapted to support and not impede a surgeon's hand movement during surgery.

18. A surgical support comprising:

a base support upon which a portion of a patient's body weight can rest, and having a left side and a right side with a head end therebetween, and a continuous slot traversing from the left side to the head end and around to the right side;

a surgeon's hand rest moveably attached to the base support at the slot such that the hand rest can attach to the base support at any location along the slot, the hand rest having freedom of motion away from and toward the base support, away from and toward a center of the base support, and angled with respect to the base support; and a patient's head rest attached to the base support and comprising a means for adjusting the height of the head rest above the base support wherein the means for adjusting is selected from the group consisting of: a jacking device, and an adjustable pin and support assembly.

19. The surgical support of claim 18, wherein the slot is a groove.

20. The surgical support of claim 18 wherein the surgeon's hand rest is adapted to support and not impede a surgeon's hand movement during surgery.

* * * * *